(12) United States Patent
Shimizu et al.

(10) Patent No.: US 10,575,903 B2
(45) Date of Patent: Mar. 3, 2020

(54) TREATMENT DEVICE AND LIVING BODY LUMEN TREATMENT METHOD

(71) Applicant: TERUMO KABUSHIKI KAISHA, Shibuya-ku, Tokyo (JP)

(72) Inventors: Katsuhiko Shimizu, Fujinomiya (JP); Yuuki Itou, Hadano (JP); Yuuichi Tada, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 364 days.

(21) Appl. No.: 15/408,167

(22) Filed: Jan. 17, 2017

(65) Prior Publication Data

US 2017/0119469 A1    May 4, 2017

Related U.S. Application Data

(63) Continuation of application No. PCT/JP2015/057862, filed on Mar. 17, 2015.

(30) Foreign Application Priority Data

Jul. 16, 2014 (JP) ................................. 2014-145734

(51) Int. Cl.
*A61B 5/00* (2006.01)
*A61B 18/22* (2006.01)
*A61B 18/00* (2006.01)

(52) U.S. Cl.
CPC .... *A61B 18/22* (2013.01); *A61B 2018/00404* (2013.01); *A61B 2018/00595* (2013.01);
(Continued)

(58) Field of Classification Search
CPC .............. A61B 18/22; A61B 2018/004; A61B 2018/00595; A61B 2018/2255; A61B 2018/2261
(Continued)

(56) References Cited

U.S. PATENT DOCUMENTS

| 5,292,320 A | 3/1994 | Brown et al. |
| 6,113,589 A | 9/2000 | Levy et al. |
| 2010/0152721 A1* | 6/2010 | Tsumanuma ........... A61B 18/24 606/15 |

FOREIGN PATENT DOCUMENTS

| JP | 2002-509777 A | 4/2002 |
| JP | 6-154239 A | 11/2005 |

(Continued)

OTHER PUBLICATIONS

International Search Report (PCT/ISA/210) dated Jun. 23, 2015; by the Japanese Patent Office as the International Searching Authority for International Application No. PCT/ JP2015/057862.
(Continued)

*Primary Examiner* — Aaron F Roane
(74) *Attorney, Agent, or Firm* — Buchanan Ingersoll & Rooney PC

(57) ABSTRACT

A treatment device is disclosed for treatment of a living body lumen. The treatment device can include an optical fiber having an emitting part that emits laser light from a side circumferential surface. Two or more grooves are provided in the emitting part at places different in a longitudinal direction of the emitting part. The two or more grooves have two or more kinds of shapes and intensities of the laser light emitted from the grooves adjacent to each other are different. A maximum region of intensity of the laser light emitted from the emitting part is located on one end side relative to a center position in the longitudinal direction of the emitting part. The intensity of the laser light emitted from the emitting part on the other end side of the emitting part relative to a position of the maximum region decreases toward the other end side.

20 Claims, 11 Drawing Sheets

(52) U.S. Cl.
CPC ............... *A61B 2018/2244* (2013.01); *A61B 2018/2255* (2013.01); *A61B 2018/2261* (2013.01)

(58) Field of Classification Search
USPC .......................................... 606/15
See application file for complete search history.

(56) References Cited

FOREIGN PATENT DOCUMENTS

| | | |
|---|---|---|
| JP | 2012-118560 A | 10/2009 |
| WO | 2008/096561 A1 | 8/2008 |

OTHER PUBLICATIONS

Written Opinion (PCT/ISA/237) dated Jun. 23, 2015, by the Japanese Patent Office as the International Searching Authority for International Application No. PCT/ JP2015/074302.
International Search Report (Form PCT/ISA/210) dated Jun. 23, 2015, by the Japanese Patent Office in corresponding International Application No. PCT/JP2015/057862 and an English Translation of the International Search Report. (9 pages).
Office Action (Notification of Reasons for Refusal) dated Jul. 31, 2018, by the Japanese Patent Office in corresponding Japanese Patent Application No. 2016-534293 and an English Translation of the Office Action. (7 pages).

\* cited by examiner

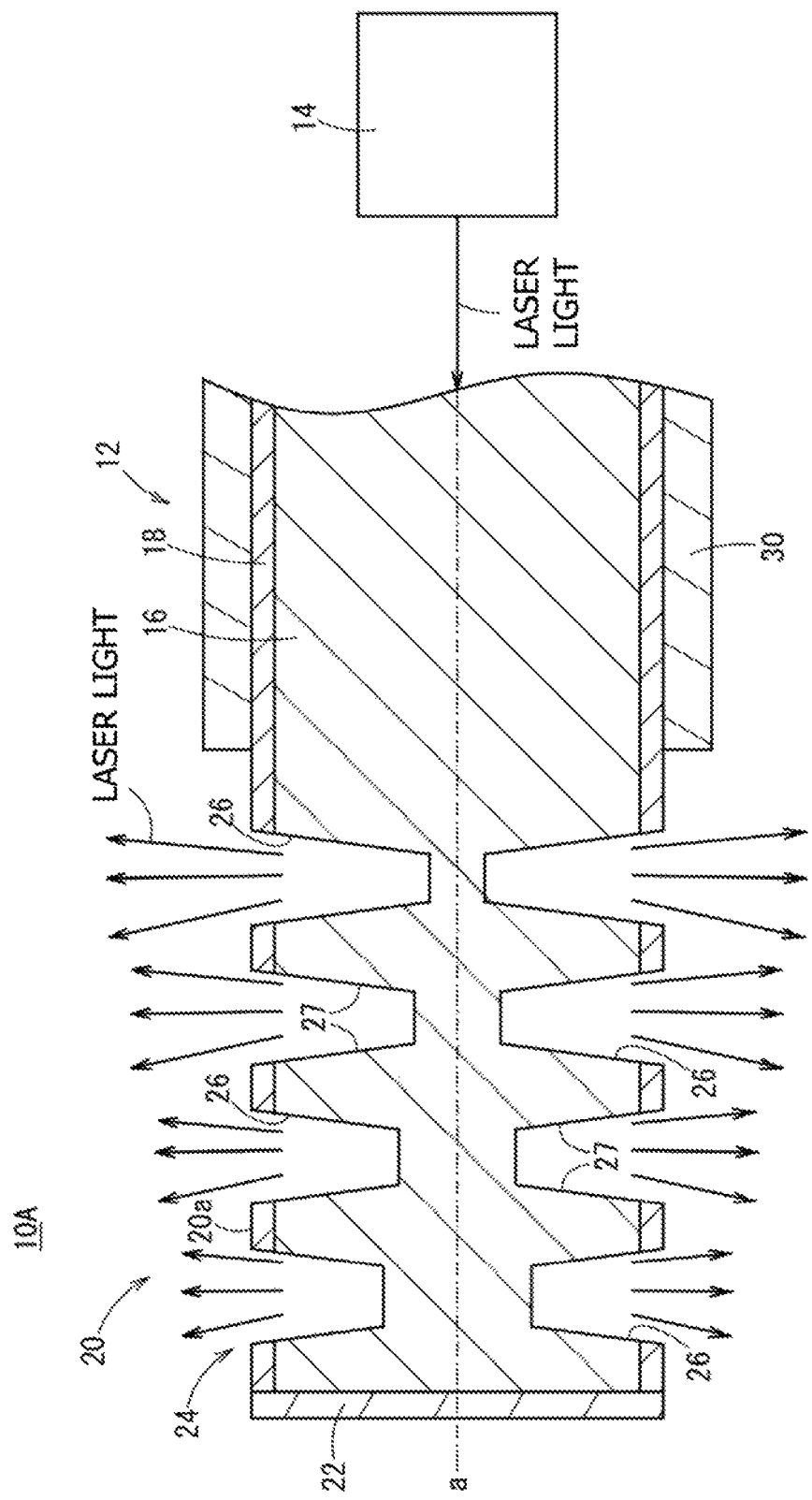

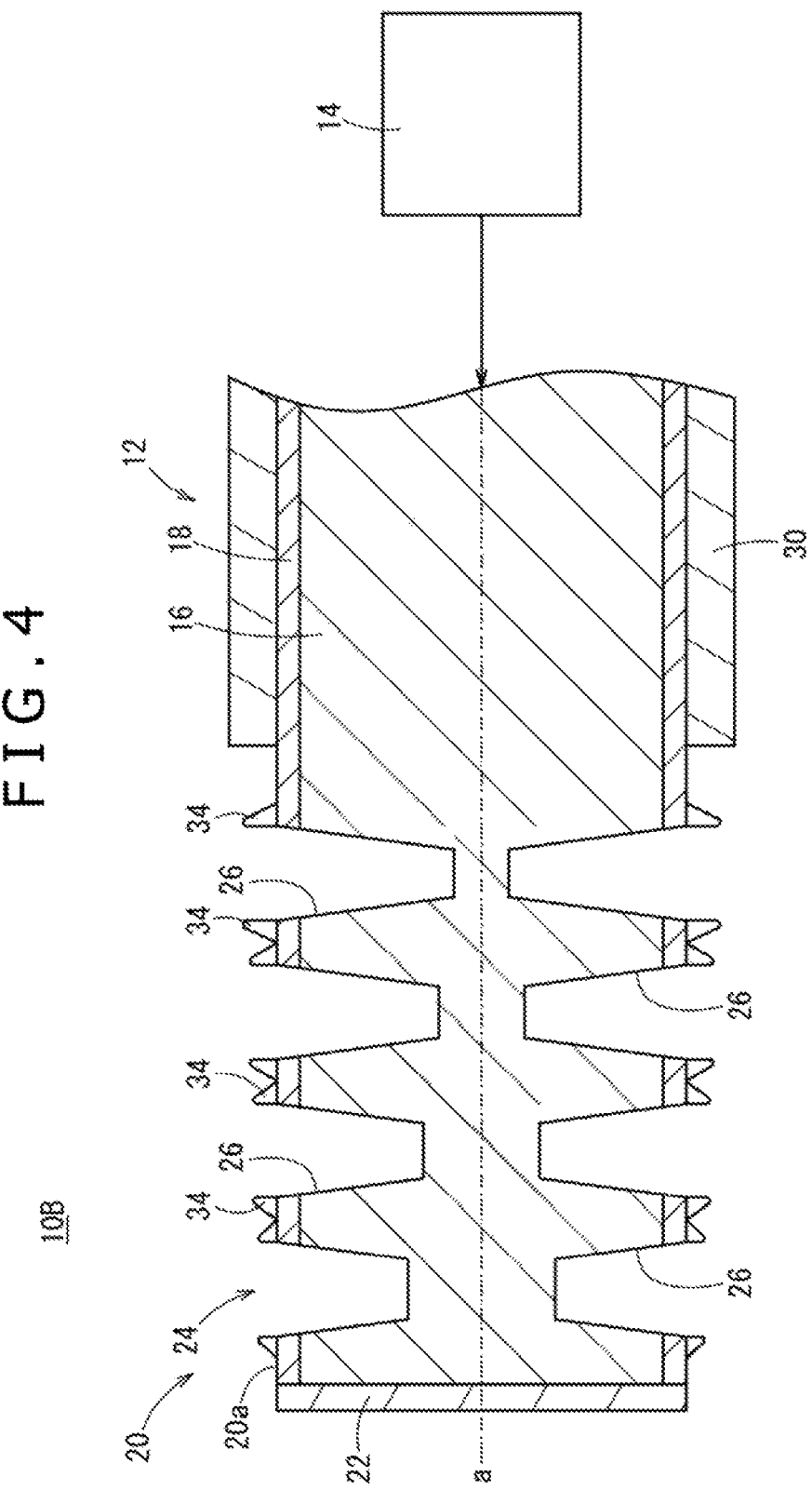

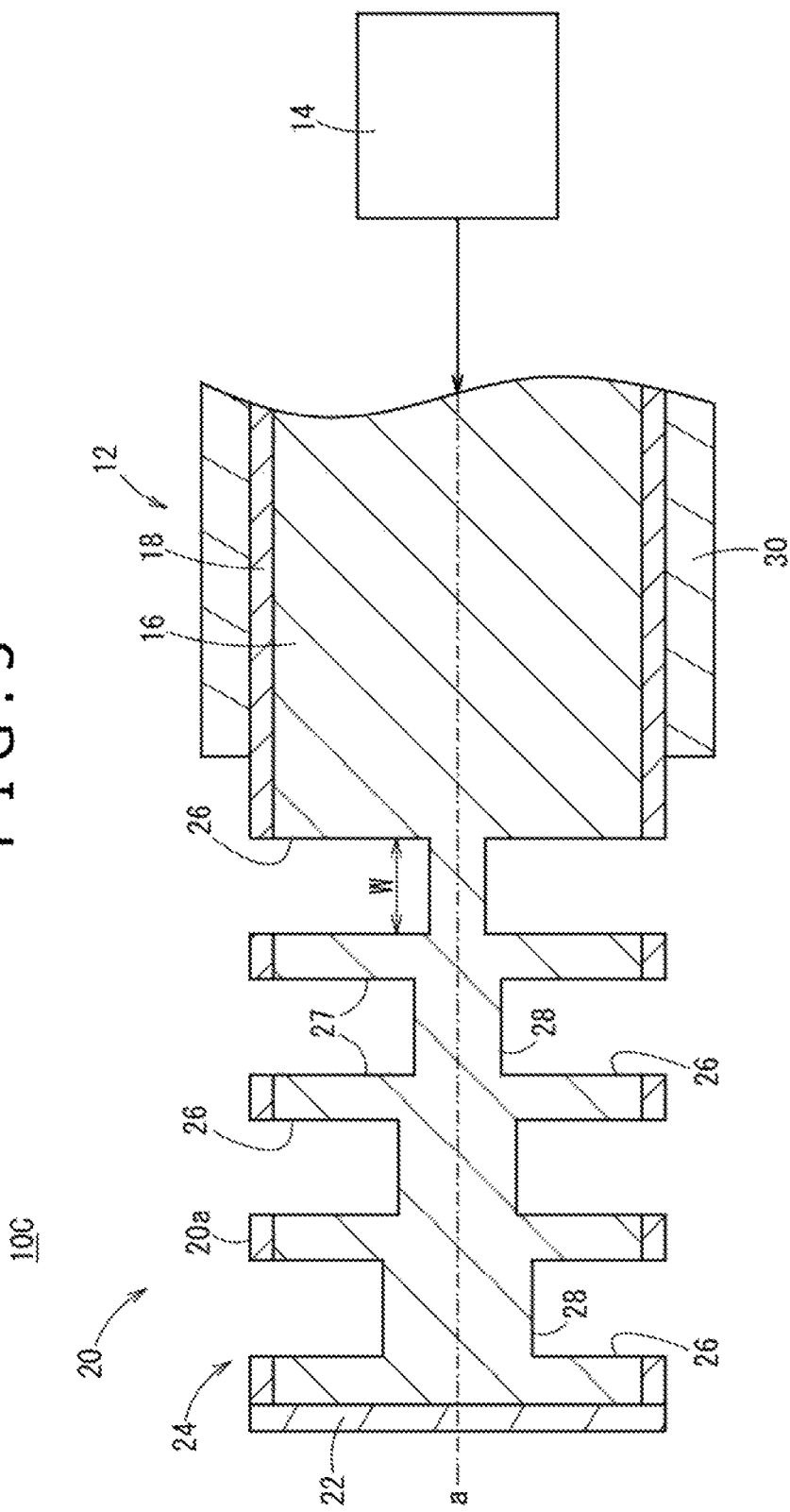

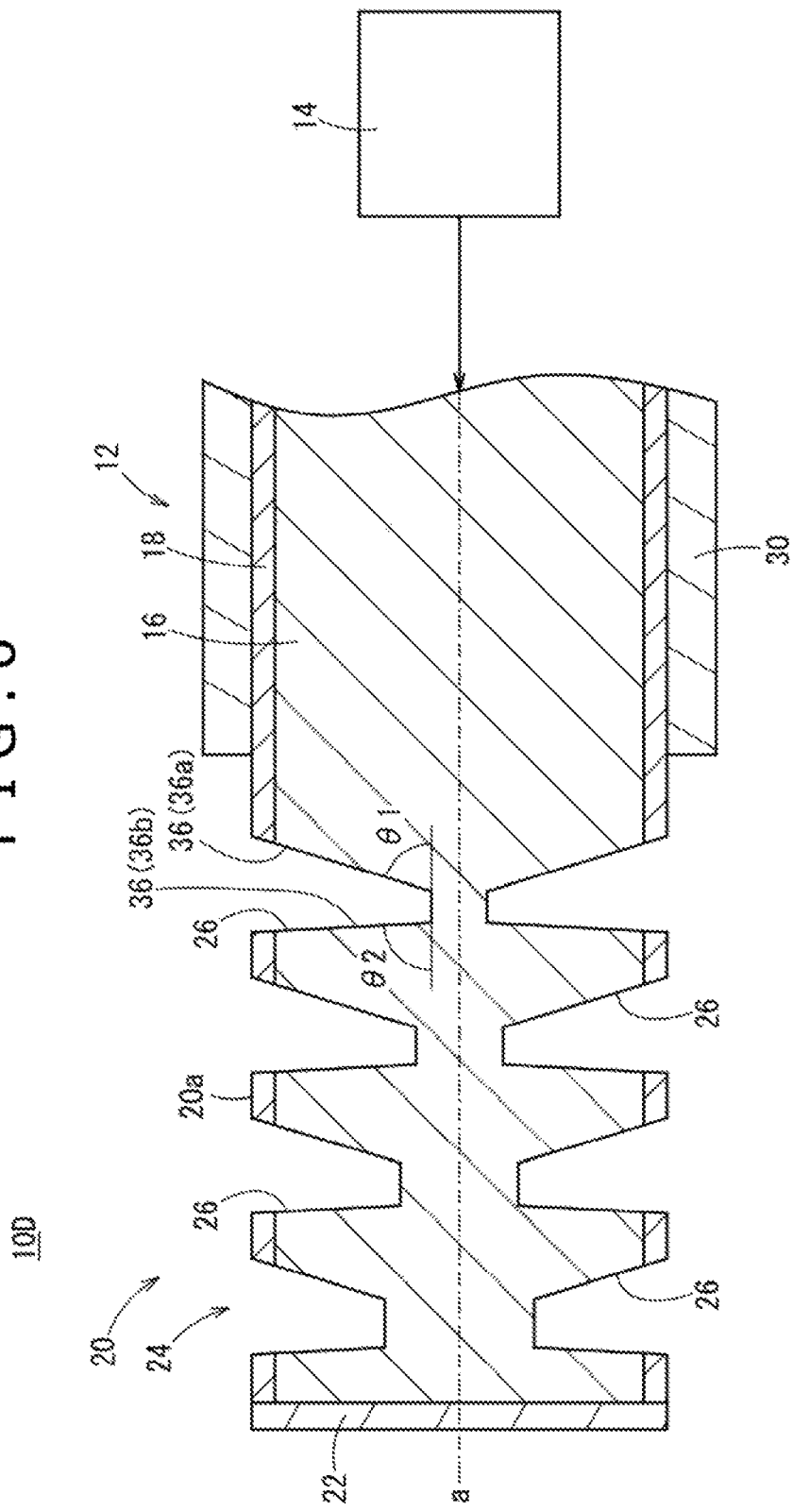

TREATMENT DEVICE AND LIVING BODY LUMEN TREATMENT METHOD

CROSS-REFERENCES TO RELATED APPLICATIONS

This application is a continuation of International Application No. PCT/JP2015/057862 filed on Mar. 17, 2015, which claims priority to Japanese Patent Application No 2014-015734 filed on Jul. 16, 2014, the entire contents of both, which are incorporated herein by reference.

TECHNICAL FIELD

The present disclosure relates to a treatment device and a living body lumen treatment method for treatment of a living body lumen.

BACKGROUND DISCUSSION

The varicose vein is a disease that occurs in living body lumens. In each vein in a living body, venous valves for returning blood to the heart against the gravity exist. If a disorder occurs in the venous valves, the backflow of blood occurs and the venous pressure becomes high, so that varicose veins develop due to dilation of veins.

Several methods have been proposed for treatment of the varicose vein, which includes a laser treatment technique of occluding a vein by heat attributed to irradiation with laser light (for example, refer to U.S. Pat. No. 7,524,316). In the laser treatment technique of the related art, an optical fiber is inserted into a vein in which a varicose vein develops. Furthermore, laser light is emitted from the distal surface of the optical fiber and a wall of the blood vessel is irradiated with the emitted laser light to cauterize the wall of the blood vessel.

However, in the laser treatment technique of the related a the laser light is emitted only from the distal surface of the optical fiber. Therefore, a wall of a blood vessel can be carbonized due to local excessive heating of the wall of the blood vessel and the wall of the blood vessel can be broken depending on the case.

SUMMARY

In accordance with exemplary embodiments, treatment devices and living body lumen treatment methods are disclosed that can properly cauterize a wall of a living body lumen, such as a wall of a blood vessel, without involving excessive heating attributed to irradiation with laser light.

A treatment device is disclosed for treatment of a living body lumen, which includes an optical fiber having an emitting part that emits laser light from a side circumferential surface. Two or more grooves are provided in the emitting part at places different in a longitudinal direction of the emitting part. The two or more grooves have two or more kinds of shapes and intensities of the laser light emitted from the grooves adjacent to each other are different.

Furthermore, another aspect of the present disclosure provides a treatment device for treatment of a living body lumen. The treatment device includes an optical fiber having an emitting part that emits laser light from a side circumferential surface. Two or more grooves are provided in the emitting part at places different in a longitudinal direction of the emitting part. A maximum region of intensity of the laser light emitted from the emitting part is located on a first end side relative to a center position in the longitudinal direction of the emitting part. The intensity of the laser light emitted from the emitting part on a second end side of the emitting part relative to a position of the maximum region decreases toward the second end side. In accordance with an exemplary embodiment, the maximum region of the intensity of the laser light includes not only a sharp peak but also a flat region having a certain level of width.

According to the aforesaid configurations, when a wall of the living body lumen is irradiated with the laser light while the treatment device is moved in the longitudinal direction (axial direction) in the living body lumen, the irradiation intensity of the laser light at each position on the wall of the living body lumen irradiated with the laser light gradually decreases. Due to this, the temperature can be promptly increased to a temperature region suitable for denaturation of tissue of the wall of the living body lumen and the temperature region suitable for denaturation can be kept for a certain period (without department from the temperature region), so that the wall of the living body lumen can be properly cauterized and denatured.

In the aforesaid treatment device, the grooves may be annular grooves that extend in a circumferential direction of the optical fiber. Due to this configuration, the laser light can be emitted from the whole circumference of the circumferential direction and thus the laser irradiation can be carried out evenly in the circumferential direction for the wall of the living body lumen. Furthermore, efficient laser irradiation can be carried out in the circumferential direction.

In the aforesaid treatment device projections that protrude outward may be provided at peripheries of the grooves in the emitting part. Due to this configuration, the laser light is readily oriented to the radial direction of the optical fiber and the laser irradiation for the wall of the living body lumen can be carried out efficiently.

In the aforesaid treatment device, the grooves may have groove forming surfaces having a certain angle with respect to an axial direction of the optical fiber, and the groove forming surface may have, in a groove depth direction, at least two surfaces different from each other in the angle with respect to the axial direction of the optical fiber. Due, to this configuration the laser light can be readily diffused in the radial direction of the optical fiber.

In the aforesaid treatment device, the surface relatively closer to a center axis line of the optical fiber in the at least two surfaces may be larger than the surface relatively farther from the center axis line in the angle with respect to the axial direction of the optical fiber. Due to this configuration the laser light can be diffused in the radial direction of the optical fiber effectively.

In the aforesaid treatment device, a ratio of groove depth of the surface relatively closer to the center axis line of the optical fiber in the at least two surfaces to groove depth of the surface relatively farther from the center axis line may decrease from a proximal side of the optical fiber toward a distal side. Due to this configuration, the light amount of the laser light emitted from the groove can be adjusted based on the ratio of the groove depth of the relatively-closer surface to the groove depth of the relatively-farther surface. Therefore, a groove structure can be designed that functions to cause the intensity of the emitted laser light to decrease from the proximal side of the optical fiber toward the distal side.

Furthermore, a living body lumen treatment method of another aspect of the present disclosure includes inserting an elongated-shaped treatment device having an emitting part that emits laser light from a side circumferential surface into a living body lumen, and irradiating a wall of the living body lumen with the laser light while the treatment device is moved in a longitudinal direction in the living body lumen. In the irradiating, irradiation with the laser light is carried out in such a manner that a temperature rise rate at each position on the wall of the living body lumen irradiated with the laser light decreases along with elapse of a procedure time.

Moreover, a living body lumen treatment method of another aspect of the present disclosure includes it inserting an elongated-shaped treatment device having an emitting part that emits laser light from a side circumferential surface into a living body lumen, and irradiating a wall of the living body lumen with the laser light while the treatment device is moved in a longitudinal direction in the living body lumen. In the irradiating, intensity of the laser light at each position on the wall of the living body lumen irradiated with the laser light shows a decrease tendency along with elapse of a procedure time after the intensity, reaches a maximum region.

According to the treatment devices and the living body lumen treatment methods of the aspects of the present disclosure, a wall of a living body lumen can be properly cauterized without involving excessive heating attributed to irradiation with laser light.

BRIEF DESCRIPTION OF THE DRAWINGS

FIG. 1 is a partly-omitted schematic diagram of a treatment device according to a first embodiment of the present disclosure.

FIG. 4 is a partly-omitted schematic diagram of a treat lent device according to a second embodiment of the present disclosure.

FIG. 5 is a partly-omitted schematic diagram of a treatment device according to a third embodiment of the present disclosure, FIG. 6 is a partly-omitted schematic diagram of a treatment device according to a fourth embodiment of the present disclosure.

DETAILED DESCRIPTION OF THE PREFERRED EMBODIMENTS

Figure 2A:
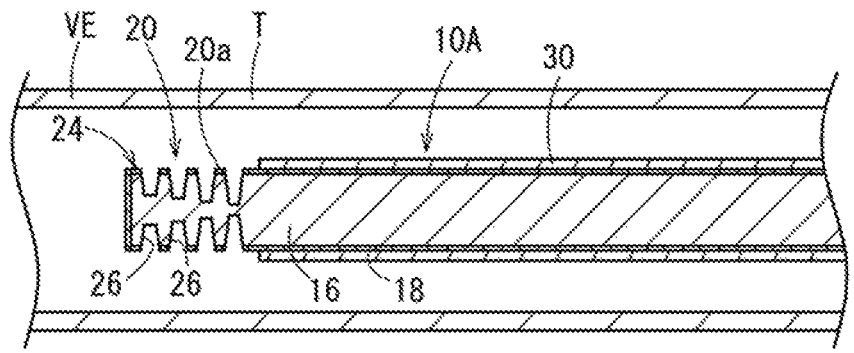
FIG. 2A is a first diagram for explaining a living body lumen treatment method.

Treatment devices, and living body lumen treatment methods according to preferred embodiments of the present disclosure will be described below with reference to the accompanying drawings.

FIG. 1 is a partly-omitted schematic diagram of a treatment device 10A according to a first embodiment of the present disclosure. The treatment device 10A can be used to occlude a living body lumen such as a blood vessel. The treatment device 10E can include an a optical fiber 12 that, can be inserted into a living body lumen and a laser light source 14 that inputs laser light to the optical fiber 12.

In accordance with an exemplary embodiment, the optical fiber 12 is an optical waveguide member having an elongated shape and flexibility. The length of the optical fiber 12 is different depending on the treatment target for the treatment device 10A. For example, if the treatment target is a varicose vein that develops in a lower extremity, the length of the optical fiber 12 can be set to approximately 500 to 4000 mm, for example.

The optical fiber 12 has a core 16 and a clad 18 that covers the core 16. In addition the optical fiber 12 has an emitting part 20 that emits laser light from a side circumferential surface 20a. The emitting part 20 is a part from a most distal position of an annular groove 26 on a most distal side to a most proximal position of the annular groove 26 on a most proximal side in the optical fiber 12, and the side circumferential surface 20a is the outer circumferential surface of the emitting part 20. Note that, in, the following description, regarding the optical fiber 12 and the constituent parts thereof, the left side in FIG. 1 will be referred to as the "distal side" and the right side in FIG. 1 will be referred to as the "proximal side." This applies also to the other drawings.

The core 16 is a part that forms a transmission path of light. The clad 18 exists around the core 16 and has a lower refractive index than the core 16. That is, the core 16 forms a higher refractive index region and the clad 18 forms a lower refractive index region. The proximal portion of the optical fiber 12 is connected to the laser light source 14. Laser light that is emitted from the laser light source 14 and incident on the optical fiber 12 travels the core 16 having the higher refractive index and total reflection is repeated at the interface between the core 16 and the clad 18 having the lower refractive index, Due to this, the laser light is transmitted without going out of the core 16 until reaching the emitting part 20.

In accordance with an exemplary embodiment, in order to prevent emission of laser light from the distal surface of the optical fiber 12, a blocking member 22 can be provided on the distal surface of the core 16. The blocking member 22 may be a reflecting member, and may be processed into a circular cone shape and be so processed as to be irradiated with light in the circumferential direction. The distal surface of the core 16 may be covered by the clad 18 instead of the blocking member 22 or with the clad 18 overlapping with the blocking member 22. From the distal surface of the core 16, laser light may leak out toward the front side without causing trouble with the procedure.

As the constituent material of the core 16 and the clad 18, materials having a high transmittance with respect to light, for example, quartz glass and resin materials (plastic), can be used.

As shown in FIG. 1 the emitting part 20 is provided near the distal portion of the optical fiber 12. In the emitting part 20, the intensity of emitted laser light decreases from one end side of the emitting part 20 toward the other end side. In the present embodiment, for example, in the emitting part 20, the intensity of emitted laser light decreases from the proximal side of the emitting part 20 toward the distal side. To realize such a function of the emitting part 20, a groove structure 24 including two or more grooves having depth toward the inside of the core 16 can be provided at the outer circumferential part of the emitting part 20. In the groove structure 24 shown in FIG. 1, the grooves gradually become shallower from the proximal side of the optical fiber 12 toward the distal side.

In the case of the present embodiment, for example, the groove structure 24 can have plural annular grooves 26 that are formed with the intermediary of intervals in the axial direction of the optical fiber 12 and extend in the circumferential direction. Each annular groove 26 reaches the inside of the core 16. The depth of the annular groove 26 decreases from the proximal side of the optical fiber 12 toward the distal side. In accordance with an exemplary embodiment, the distance between the annular groove 26 and a center axis line a increases from the proximal side of the optical fiber 12 toward the distal side. The axial direction of the optical fiber 12 is the direction along the center axis line a of the optical fiber 12, for example, the long-axis direction of the optical fiber 12. Note that, in a modification example of the groove structure 24, on the proximal side relative to the annular groove 26 having the largest groove depth, the annular groove 26 having a smaller groove depth than the annular groove 26 may be provided. Furthermore, when the annular grooves 26 have the same angle of a sidewall 27 with respect to the center axis line a and the radiation ports of the groove structures 24 (on the opposite side to the center axis line a of the optical fiber 12 in annular grooves 26) are oriented in the same direction, a part it which laser light emitted from the adjacent annular grooves 26 overlap with each other in a wide range can be obtained.

In the case of the present embodiment, the width of each annular groove 26 forming the groove structure 24 (groove width along the axial direction of the optical fiber 12) decreases toward the center axis line a of the optical fiber 12. In FIG. 1, the shape of each annular groove 26 in a longitudinal section along the center axis line a of the optical fiber 12 is a trapezoidal shape. However, the shape may be a V-shape having the apex on the side of the center axis line a. Furthermore, the groove structure 24 may have one or more trapezoidal annular grooves 26 and one or re V-shaped annular grooves 26.

In FIG. 1, in the plural annular grooves 26, the aperture widths of the annular grooves 26 along the axial direction of the optical fiber 12 are all the same and the angles of the sidewall 27 (groove forming surface) with respect to the center axis line a are also all the same. Similarly to a fifth embodiment to be described later, the angle of the groove forming surface with respect to the axial direction may decrease from the distal side of the optical fiber 12 toward the proximal side. Furthermore, similarly to a sixth embodiment to be described later, the aperture width of the respective annular grooves 26 forming the groove structure 24 along the axial direction of the optical fiber 12 at the outer circumferential part of the emitting part 20 may decrease from the proximal side of the optical fiber 12 toward the distal side.

When laser light that is emitted from the laser light source 14 and is incident on the optical fiber 12 is transmitted to the emitting part 20 of the optical fiber 12, the laser light is reflected and refracted to the outer circumferential side of the emitting part 20 by the groove structure 24 (plural annular grooves 26) provided in the emitting part 20. As a result, the laser light is deflected to the radial direction and is discharged from the whole circumference of the side circumferential part of the emitting part 20. At this time, the depth of the plural annular grooves 26 decreases from the proximal side of the optical fiber 12 toward the distal side, and the intensity of the laser light discharged in the radial direction is higher when the groove is deeper. Therefore, in the emitting part 20, the intensity of the emitted laser light gradually (in a stepwise manner) decreases from the proximal side of the optical fiber 12 toward the distal side.

In accordance with an exemplary embodiment, to be exact, in the laser light emitted from the annular groove 26 not only laser light in the direction perpendicular to the center axis line a but also laser light emitted in a direction inclined from the direction perpendicular to the axis line due to reflection of the laser light in the annular groove 26 exists. For this reason, in the intensity profile of the laser light emitted from the emitting part 20, a place at which the intensity is low exists on the proximal side relative to the place of the maximum intensity. Therefore, in the emitting part 20 of the aforesaid optical fiber 12 the maximum region of the intensity of the laser light emitted from the emitting part 20 exists on the proximal side relative to the center position of the emitting part 20 in the longitudinal direction for example, at a position near the proximal end of the emitting part 20), and the intensity of the emitted laser light decreases from the position of the aforesaid maximum region toward the distal side of the emitting part 20. Note that the maximum region of the intensity of the laser light emitted from the emitting part 20 can include not only a sharp peak but also a flat region having a certain level of width. Furthermore, for example, the maximum region of the intensity of the emitted laser light can be a part in which laser light emitted from the plural annular grooves 26 overlap with each other.

In addition, in accordance with an exemplary embodiment, the optical fiber 12 can include a cover member 30 that covers the clad 18. The cover member 30 is a component for protecting the core 16 and the clad 18 and is composed of a resin material, for example.

The laser light source 14 is not particularly limited as long as it can be applied to treatment of a living body lumen. For example, a semiconductor laser apparatus a carbon dioxide gas laser apparatus, or an excimer laser apparatus can be used as the laser light source 14. The wavelength of applied laser light, for example, laser light generated by the laser light source 14, can be selected from wavelengths of 810, 940, 1064, 1320, 1470, and 2000 nm, for example. The oscillation system of the laser light may be a pulse laser system in which a pulse-like output is oscillated at a certain repetition frequency, or may be a continuous wave laser system in which laser light is, continuously output.

Next, by taking treatment of a varicose vein as an example, a treatment method (living body lumen treatment method) by use of the treatment device 10A will be described.

The treatment device 10A configured as described above is prepared. Next, as shown in FIG. 2A, an insertion step of causing the emitting part 20 provided at the distal portion of the treatment device 10A to reach a treatment site T (target site) by inserting the treatment device 10A into a vein VE is carried out. In this case for example, the patient is punctured by an introducer sheath and the treatment device 10A is inserted into the vein VE in which a varicose vein develops with the intermediary of this introducer sheath. In, the insertion, the treatment device 10A can be inserted while the distal end position of the treatment device 10A is checked in an ultrasound-guided manner. Then, as shown in FIG. 2A, the distal portion of the treatment device 10A is caused to, reach the treatment site T of the vein VE.

Figure 2B:
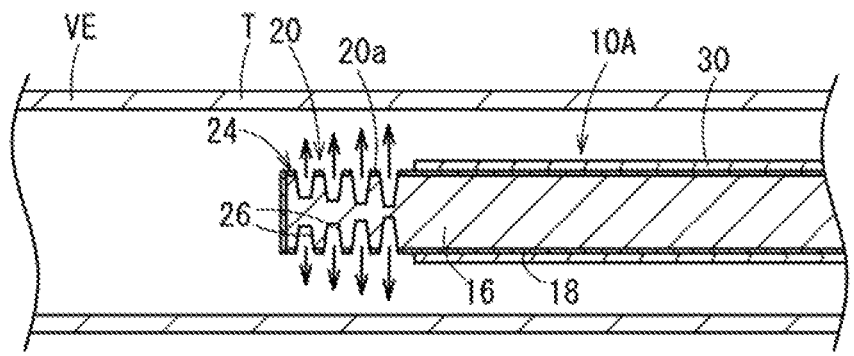
FIG. 2B is a second diagram for explaining the living body lumen treatment method.
Figure 2C:
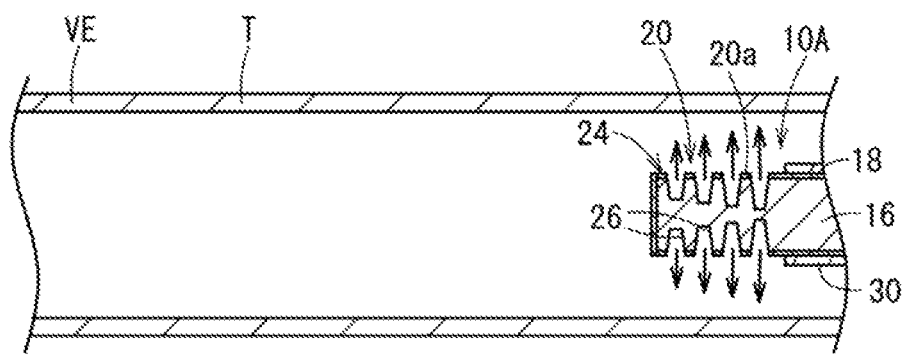
FIG. 2C is a third diagram for explaining the living body lumen treatment method.

Next, in order to carry out a procedure for occlusion for the vein VE, an irradiation step of cauterizing a vein wall by heat attributed to irradiation with laser light is carried out. For example, in the irradiation step, as shown in FIG. 28 and FIG. 2, the vein wall is irradiated with the laser light while the treatment device 10A (emitting part 20) is moved in the proximal direction in the vein VE (living body lumen). The vein can be occluded by denaturing tissue of the vein wall by the irradiation with the laser light. Note that, even when the distance between the vein wall (wall of the blood vessel) and the optical fiber 12 is large and the vein wall not irradiated with the laser light due to absorption of the laser light by blood, the laser light heats the blood or water in the blood and thereby the heated blood or the heated water in the blood heats the vein wall.

In this case, in the treatment device 10A, the maximum region of the intensity of the laser light emitted by the emitting part 20 exists on the proximal side relative to the center position of the emitting part 20, and the configuration is so made that the intensity of the emitted laser light decreases from the maximum region toward the distal side of the emitting part 20. For this reason, when the vein wall is irradiated with the laser light while the treatment device 10A is moved in the proximal direction in the vein VE, the irradiation intensity of the laser light at each position on the vein wall irradiated with the laser light gradually decreases (shows a decrease tendency) along with the elapse of the procedure time. Therefore, excessive temperature rise of the vein wall can be suppressed and the vein wall can be effectively cauterized by heat attributed to the irradiation with the laser light. Note that the movement of the treatment device 10A in the vein VE may be at a constant speed.

In this case, the laser light is emitted in the radial direction from the whole circumference of the emitting part 20 because the groove structure 24 that is provided in the emitting part 20 and has an annular shape extends across the whole circumference of the emitting part 20. Therefore, the whole circumference of the vein wall is irradiated with the laser light and thus the procedure based on the irradiation with the laser light can be accomplished evenly in the circumferential direction. Furthermore, the procedure can be efficiently accomplished over the whole circumference.

After such cauterization for the vein VE is carried out in the desired range, the emission of the laser light from the emitting part 20 is stopped and the treatment device 10A is withdrawn from the inside of the body (vein VE) (withdrawal step).

Note that, also when treatment devices 10B to 10H according to other embodiments to be described later are used, the living body lumen treatment method can be carried out similarly to the aforesaid description.

As described above, according to the treatment device 10A and the living body lumen treatment method in accordance with the present embodiment, when a wall of a living body lumen is irradiated with laser light while the treatment device 10A is moved in the proximal direction in the living body lumen, the irradiation intensity of the laser light at each position on the wall of the living body lumen irradiated with the laser light gradually decreases. Due to this, the temperature can be promptly increased to a temperature region suitable for denaturation of tissue of the wall of the living body lumen and the temperature region suitable for denaturation can be kept for a certain period (without department from the temperature region), so that the wall of the living body lumen can be properly cauterized and denatured.

In the case of the present embodiment, the sidewalls 27 of each annular groove 26 are inclined with respect to the axial direction of the optical fiber 12 and therefore laser light that reaches the groove structure 24 is readily diffused in the radial direction of the optical fiber 12. Thus, the laser light can be effectively emitted from the side circumferential surface 20a of the emitting part 20 and the treatment efficiency can be enhanced.

Figure 3A:
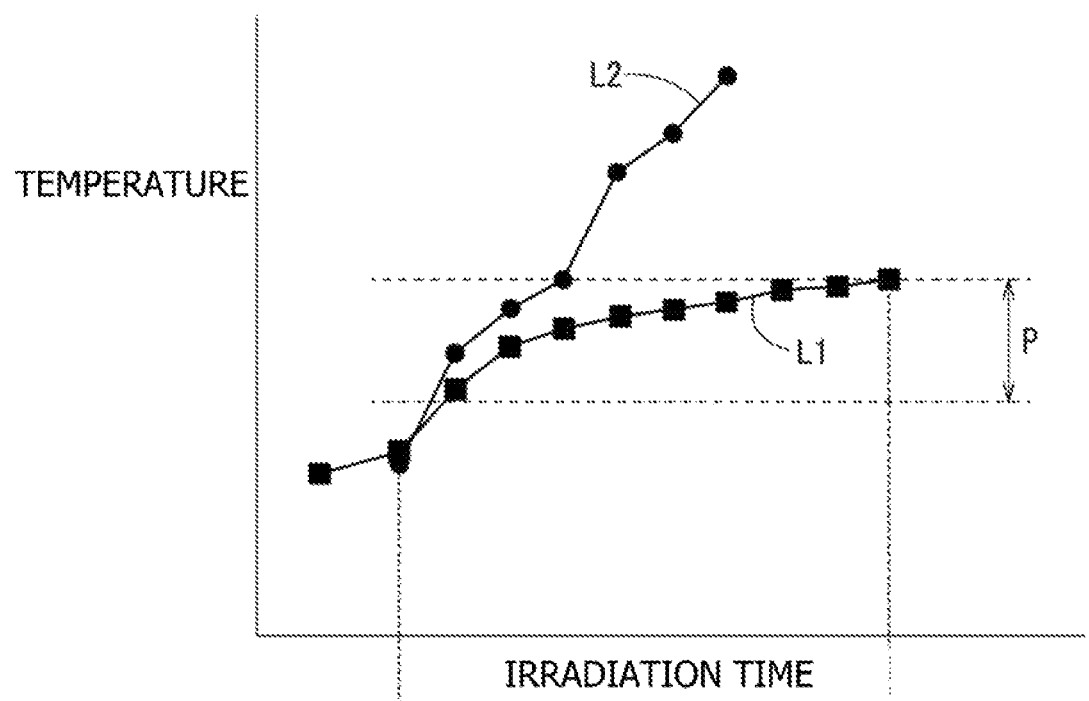
FIG. 3A is a graph showing the relationship between the irradiation time of laser light at a specific position on a wall of a blood vessel and the temperature of the wall of the blood vessel regarding a working example of the disclosure and a comparative example.

Here, FIG. 3A is a graph showing the relationship between the irradiation time of laser light (procedure time) at a specific position on a wall of a blood vessel and the temperature of the wall of the blood vessel regarding a working example of the present disclosure and a comparative example (related art). A curve line L1 shows the working example of the present disclosure and a curve line L2 shows the comparative example. In the comparative example the wall of the blood vessel was irradiated with the laser light emitted in the circumferential direction from the distal surface of an optical fiber without decreasing the light intensity.

Figure 3B:
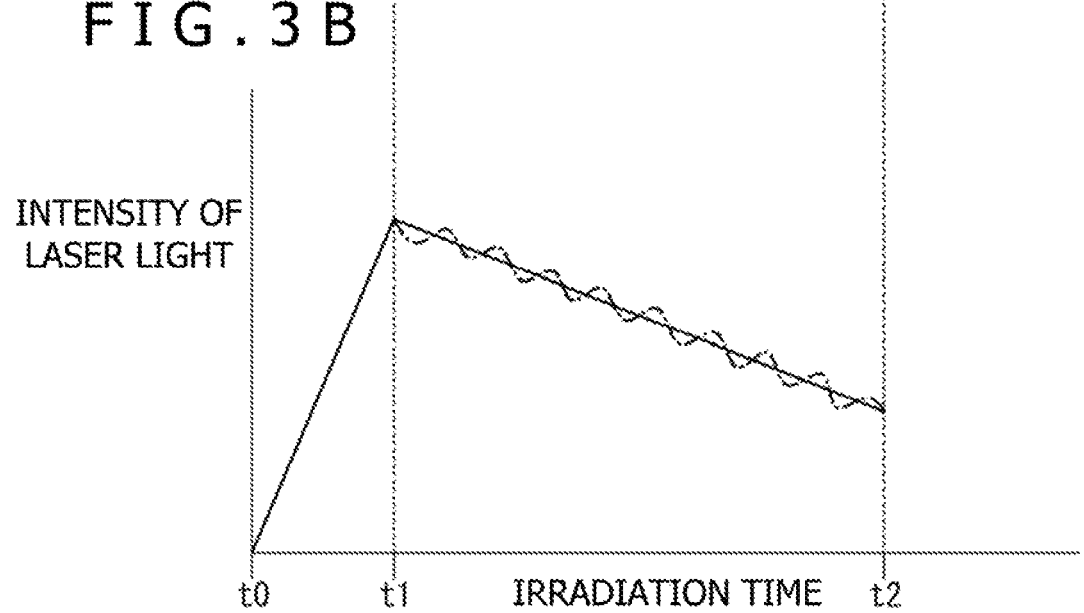
FIG. 3B is a graph showing the relationship between the irradiation time of the laser light at the specific position on the wall of the blood vessel and the intensity of the laser light regarding the working example of the present disclosure.

FIG. 3B is a graph showing the relationship between the irradiation time of the laser light (procedure time) at the specific position on the wall of the blood vessel and the intensity of the laser light regarding the working example of the present disclosure.

As shown in FIG. 3A, in the comparative example, the temperature of the wall of the blood vessel rose substantially linearly along with the elapse of the irradiation time and the temperature reached a temperature region surpassing a proper temperature region P in a short time. For this reason, the wall of the blood vessel was excessively heated and tissue was carbonized. In contrast, in the working example of the present disclosure, the temperature rise became gentler along with the elapse of the irradiation time (temperature rise rate decreased) in the proper temperature region P of the procedure, and the temperature was kept in the proper temperature region P for a somewhat long time. For this reason, carbonization of tissue due to excessive heating of the wall of the blood vessel did not occur. The proper temperature region P is a temperature region in which the wall of the blood vessel can be cauterized without being carbonized and the blood vessel can be occluded by the cauterize ion, and is a temperature range of 50° C. to 99° C., for example.

Note that, to be exact, as shown in FIG. 3B, the intensity of the laser light at each position on the wall of the blood vessel irradiated with the laser light risen in an initial period of the irradiation (t0 to t1) and decreases after reaching the maximum intensity at the time t1. This is because a part in which the intensity of the laser light is low exists on the proximal side relative to the peak position of the intensity of the laser light emitted from the emitting part 20 as described above. For this reason, the decrease in the temperature rise rate along with the elapse of the procedure time is after the period in which the intensity of the laser light rises in FIG. 3B (after the time t1, at which the intensity of the laser light reaches the maximum intensity).

Furthermore, for details as shown by a virtual line in FIG. 38, after reaching the maximum intensity (after t1), the intensity of the laser light at each position on the wall of the blood vessel does not constantly decrease along with the elapse of the procedure time but decreases with repetition of fluctuation to higher and lower intensity. For example, the intensity of the laser light increases at an overlapping part in which laser light emitted from grooves adjacent in the axial direction in the groove structure 24 overlap with each other on the wall of the blood vessel, whereas the intensity of the laser light decreases at a part in which laser light do not overlap with each other on the wall of the blood vessel. For example, the overlapping part of laser light and the part in which laser light do not overlap alternately repeat. When the intensity of the laser light decreases, the intensity of the overlapping part of the laser light also decreases. That is, the intensity of the laser light at each position on the wall of the living body lumen irradiated with the laser light shows a decrease tendency along with the elapse of the procedure time after the intensity reaches the maximum region.

In the case of the present embodiment, the groove structure 24 having depth toward the inside of the core 16 is provided at the outer circumferential part of the emitting part 20 and the groove depth of the groove structure 24 decreases from the proximal side of the optical fiber 12 toward the distal side. Due to this configuration, the emitting part 20 in which the intensity of emitted laser light decreases from the proximal side of the optical fiber 12 toward the distal side can be easily configured.

In the case of the present embodiment, the groove structure 24 has plural annular grooves that are formed with the intermediary of intervals in the axial direction of the optical fiber 12 and extend in the circumferential direction. Due to this configuration, laser light can be emitted from the whole circumference of the circumferential direction and thus efficient laser irradiation can be carried out for an inner wall of a living body lumen.

FIG. 4 is a partly-omitted schematic diagram of a treatment device 10B according to a second embodiment of the present disclosure. In the treatment device 10B according to the second embodiment, an element that exerts the same or similar function and effect as the treatment device 10A according to the first embodiment is given the same reference numeral and detailed description thereof is omitted. This applies also to the other embodiments to be described later.

The treatment device 10B is obtained by adding projections 34 to the optical fiber 12 of the treatment device 10A according to the first embodiment. In accordance with an exemplary embodiment, on a side circumferential surface 20a of an emitting part 20, the projections 34 that protrude outward (outward in the radial direction) are provided at the periphery of each annular groove 26 forming a groove structure 24 (in the example shown in FIG. 4 on both sides of each annular groove 26). Each projection 34 may be formed into an annular shape that extends in the circumferential direction along the annular groove 26 or may be formed into one or more arc shapes that extend in the circumferential direction along the annular groove 26.

According to the treatment device 10B having such projections 34, laser light is readily oriented to the radial direction of the optical fiber 12 and laser irradiation for a wall of a living body lumen such as a wall of a blood vessel, can be carried out more efficiently. Due to the provision of the projections 34 on the extension of (outside of) the groove structure 24, the area of the sidewalls 27 becomes larger and more laser light of the optical fiber 12 can be reflected and refracted to be radiated. This allows emission of laser light with higher intensity. Note that the periphery of the groove at which the projection is provided is both sides of the aperture of the annular groove if the groove is the annular groove 2 and is a part surrounding the aperture of the groove if the groove is a groove having a triangular pyramid shape, for example.

Furthermore, the protrusion height of the projection 4 gradually decreases from the proximal side of the optical fiber 12 toward the distal side. Due to this configuration, the directionality to the radial direction of the optical fiber 12 can be adjusted based do the protrusion height of the projection 34 at the stage of design. Therefore, the groove structure 24 can be designed that functions to cause the intensity of emitted laser light to decrease from the proximal side of the optical fiber 12 toward the distal side.

Note that, regarding the respective constituent parts common with the first embodiment in the second embodiment, operation and effect that are the same as or similar to operation and effect provided by these respective common constituent parts in the first embodiment are achieved. This applies also to the other embodiments to be described later.

FIG. 5 is a partly-omitted schematic diagram of a treatment device 10C according to a third embodiment of the present disclosure. In the treatment device 10C, the point that the depth of annular grooves 26 provided as plural grooves decreases from the proximal side of an optical fiber 12 toward the distal side is the same as the above-described treatment device 10A.

In the treatment device 10C, each annular groove 26 has sidewalls 27 that are perpendicular to a center axis line a and are opposed in parallel to each other and a bottom wall 28 that couples the sidewalls 27 with each other. Each annular groove 26 has a rectangular shape in a longitudinal section along the center axis line a of the optical fiber 12 as shown in FIG. 5. The longitudinal sectional shape of each annular groove 26 along the center axis line a of the optical fiber 12 may be a U-shape.

In the case of the present embodiment, in the plural annular grooves 26, widths W along the axial direction of the optical fiber 12 at the outer circumferential part of an emitting part 20 are all the same.

FIG. 6 is a partly-omitted schematic diagram of a treatment device 10D according to a fourth embodiment of the present disclosure. In the treatment device 10D, the point that the depth of annular grooves 26 provided as plural grooves decreases from the proximal side of an optical fiber 12 toward the distal side is the same as the above-described treatment device 10A.

In the treatment device 10D, the width of each annular groove 26 forming a groove structure 24 decreases toward a center axis line a of the optical fiber 12. Each annular groove 26 has groove forming surfaces 36 opposed to each other in the axial direction of the optical fiber 12. In each annular groove 26 an angle θ1 of a groove forming surface 36a on the proximal side with respect to the axial direction of the optical fiber 12 is smaller than an angle 92 of a groove forming surface 6b on the distal side with respect to the axial direction of the optical fiber 12.

According to the treatment device 10D configured in this manner, laser light is diffused in the radial direction of the optical fiber 12 more effectively.

Figure 7:
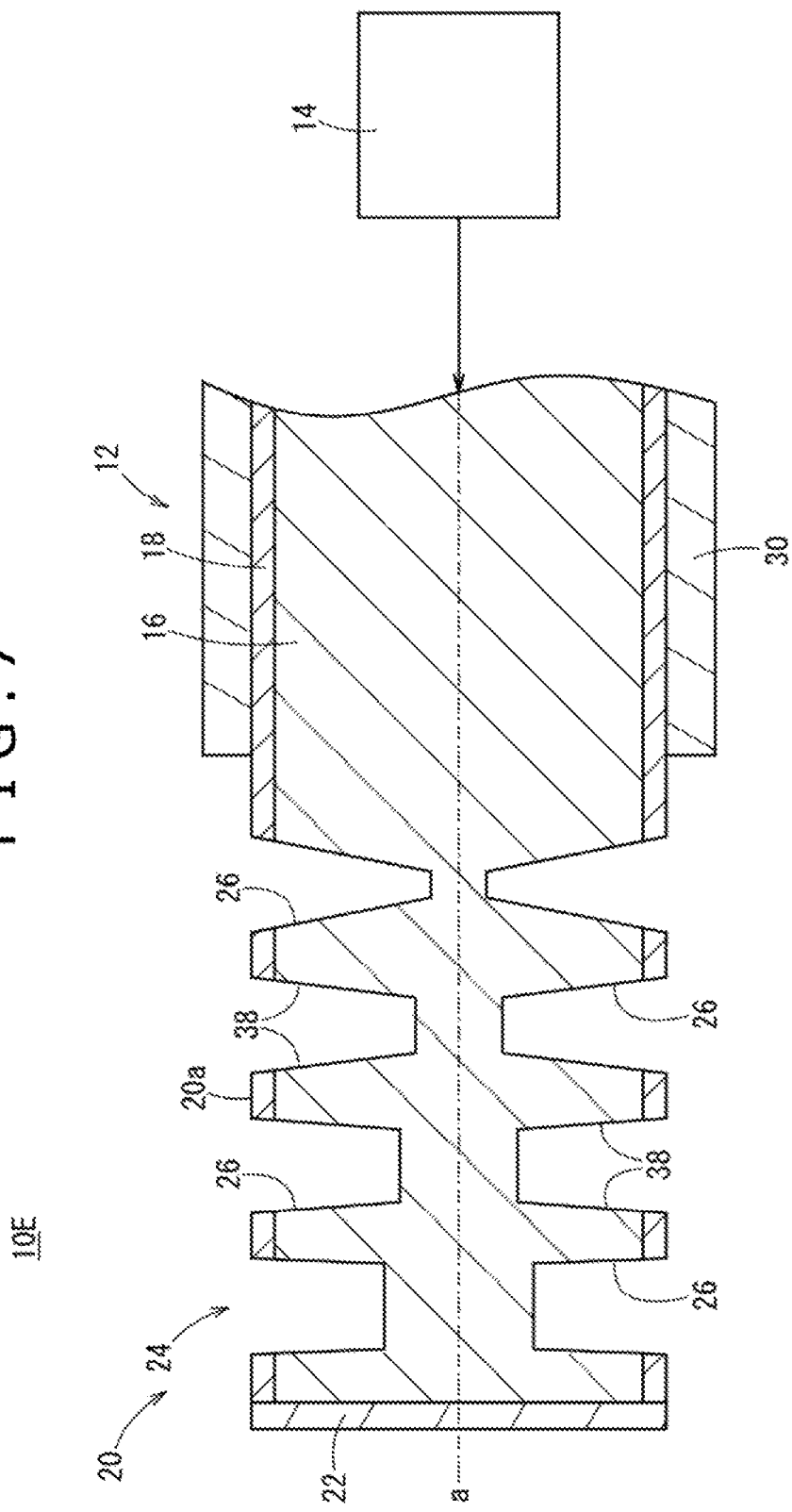
FIG. 7 is a partly-omitted schematic diagram of a treatment device according to a fifth embodiment of the present disclosure.

FIG. 7 is a partly-omitted schematic diagram of a treatment device 10E according to a fifth embodiment of the present disclosure. In the treatment device 10E, the point that the depth of annular grooves 26 provided as plural grooves decreases from the proximal side of an optical fiber 12 toward the distal side is the same as the above-described treatment device 10A.

In the treatment device 10E the width of each annular groove 26 forming a groove structure 24 decreases toward a center axis line a of the optical fiber 12. Each annular groove 26 has groove forming surfaces 38 opposed to each other in the axial direction of the optical fiber 12. The angle of the groove forming surface 38 with respect to the axial direction decreases from the distal side of the optical fiber 12 toward the proximal side.

According to the treatment device 10E configured in this manner, the light mount of laser light emitted from the annular groove 26 can be adjusted based on the angle of the groove forming surface 38 with respect to the axial direction. Therefore, the groove structure 24 can be designed that functions to cause the intensity of emitted laser light to decrease from the proximal side of the optical fiber 12 toward the distal side.

Figure 8:
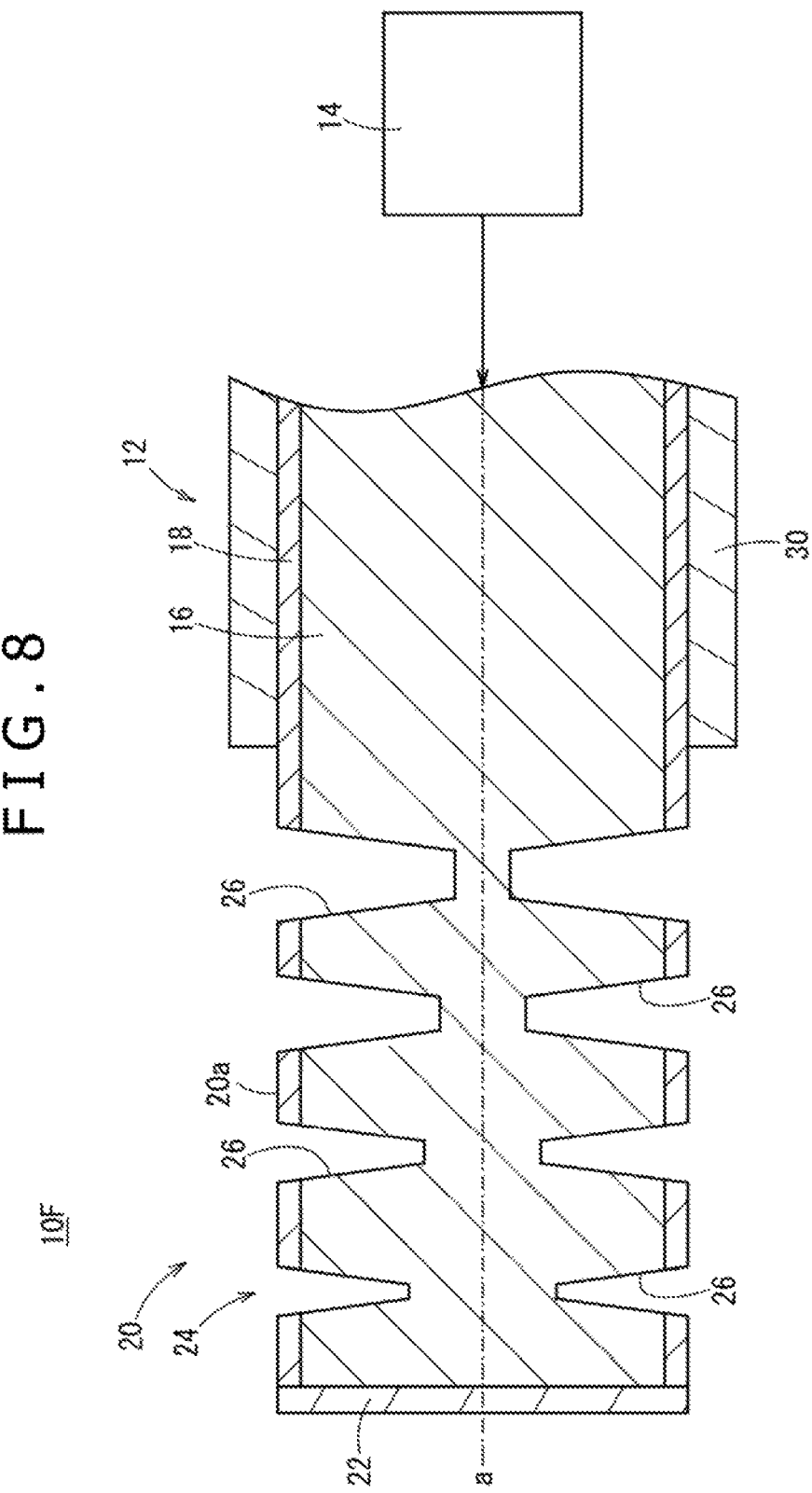
FIG. 8 is a partly-omitted schematic diagram of a treatment device according to a sixth embodiment of the present disclosure.

FIG. 8 is a partly-omitted schematic diagram of a treatment device 10F according to a sixth embodiment of the present disclosure. In the treatment device 10F, the point that the depth of annular grooves 26 provided as plural grooves decreases from the proximal side of an optical fiber 12 toward the distal side is the same as the above-described treatment device 10A.

In the treatment device 10F the width of each annular groove 26 forming a groove structure 24 decreases toward a center axis line a of the optical fiber 12. The aperture width of the respective annular grooves 26 forming the groove structure 24 along the axial direction of the optical fiber 12 at the outer circumferential part of an emitting part 20 decreases from the proximal side of the optical fiber 12 toward the distal side.

According to the treatment device 10F configured in this manner, the light amount of laser light emitted from the annular groove 26 can be adjusted based on the magnitude of the aperture width of the annular groove 26. Therefore, the groove structure 24 can be designed that functions to cause the intensity of emitted laser light to decrease from the proximal side of the optical fiber 12 toward the distal side.

Figure 9:
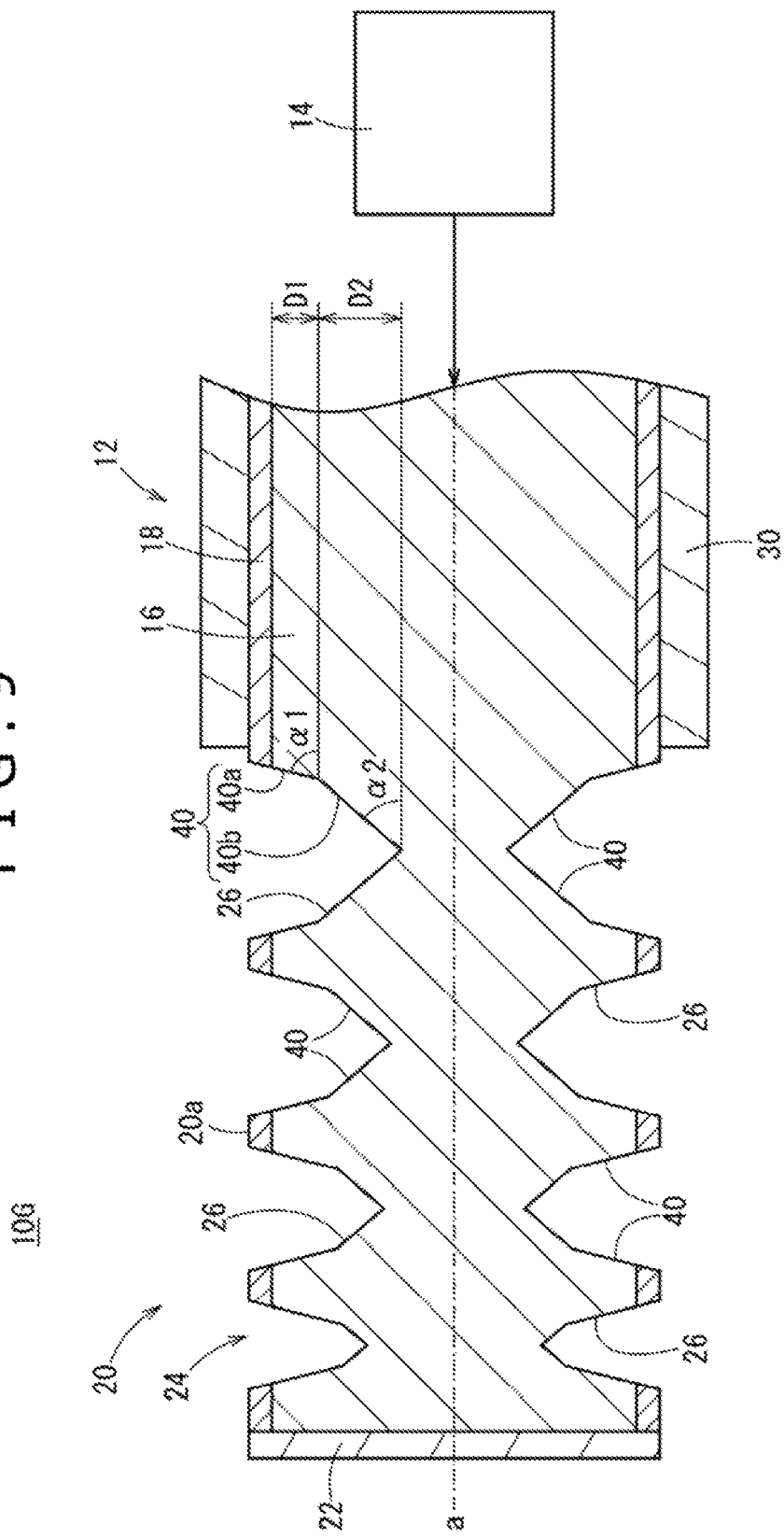
FIG. 9 is a partly-omitted schematic diagram of a treatment device according to a seventh embodiment of the present disclosure.

FIG. 9 is a partly-omitted schematic diagram of a treatment device 10G according to a seventh embodiment of the present disclosure. In the treatment device 10G the point that the depth of annular grooves 26 provided as plural grooves decreases from the proximal side of an optical fiber 12 toward the distal side is the same as the above-described treatment device 10A.

In the treatment device 10G, the width of each annular groove 26 forming a groove structure 24 decreases toward a center axis line a of the optical fiber 12. Each annular groove 26 forming the groove structure 24 has groove forming surfaces 40 having an angle with respect to the axial direction of the optical fiber 12. The groove forming surface 40 has, in the groove depth direction, at least two surfaces 40a and 40b different from each other in the angle with respect to the axial direction of the opt cal fiber 12. That is, the groove forming surface 40 bends in the middle in the groove depth direction. Due to this configuration, laser light can be readily diffused in the radial direction of the optical fiber 12 in each annular groove 26.

Furthermore, in the treatment device 10G, an angle α2 with respect to the axial direction of the optical fiber 12 regarding the surface 40b relatively closer to the center axis line a in at least two surfaces 40a and 40b forming the groove forming surface 40 is larger than an angle α1 of the surface 40a relatively farther from the center axis line a with respect to the axial direction of the optical fiber 12. Due to this configuration, laser light is diffused in the radial direction of the optical fiber 12 more effectively.

Moreover, in the treatment device 10G, the ratio of a groove depth D2 of the surface 40b relatively closer to the center axis line a of the optical fiber 12 in at least two surfaces 40a and 40b to a groove depth D1 of the surface 40a relatively farther from the center axis line a decreases from the proximal side of the optical fiber 12 toward the distal side. Due to this configuration, the light amount of laser light emitted from the annular groove 26 can be adjusted based on the ratio of the groove depth D2 of the relatively-closer surface 40b to the groove depth D1 of the relatively-farther surface 40a. Therefore, the groove structure 24 can be designed that functions to cause the intensity of emitted laser light to decrease from the proximal side of the optical fiber 12 toward the distal side.

Figure 10:
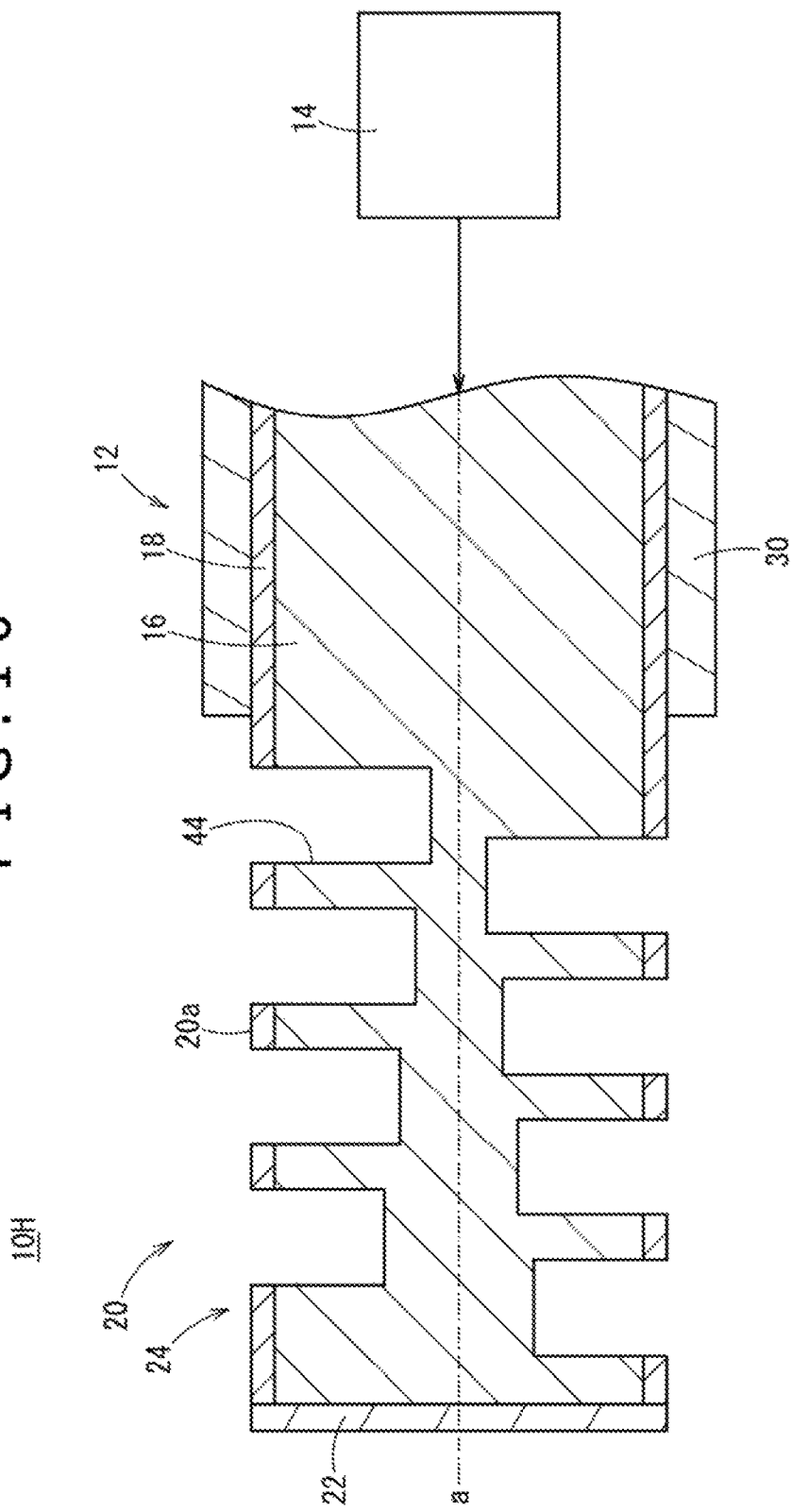
FIG. 10 is a partly-omitted schematic diagram of a treatment device according to an eighth embodiment of the present disclosure.

FIG. 10 is a partly-omitted schematic diagram of a treatment device 10H according to an eighth embodiment of the present disclosure. In the treatment device 10H a groove structure 24 has at least one spiral groove 44 that extends in a spiral manner at the outer circumferential part of an emitting part 20. The groove depth of the spiral groove 44 gradually (continuously or in a stepwise manner) decreases from the proximal side of an optical fiber 12 toward the distal side.

Therefore, as with the treatment, device 10A, when a wall of a living body lumen is irradiated with laser light while the treatment device 10H is moved in the proximal direction in the living body lumen, the irradiation intensity of the laser light at each position on the wall of the living body lumen irradiated with the laser light gradually decreases which can help suppress excessive temperature rise of the wall of the living body lumen and effectively cauterize the wall of the living body lumen.

Furthermore, also by the treatment device 10H having the spiral groove 44 in the emitting part 20, laser light can be emitted from the whole circumference of the circumferential direction and thus efficient laser irradiation can be carried out for a wall of a living body lumen as with the aforementioned treatment device 10A.

Note that plural spiral grooves 44 may be provided. If the plural spiral grooves 44 are provided, the spiral grooves 44 may be disposed to be lined up in different regions in the axial direction of the optical fiber 12 or may be disposed to draw a multiple spiral. Furthermore, in the treatment device 10H, characteristics a the aforementioned treatment devices 10A to 10G may be arbitrarily combined.

Figure 11:
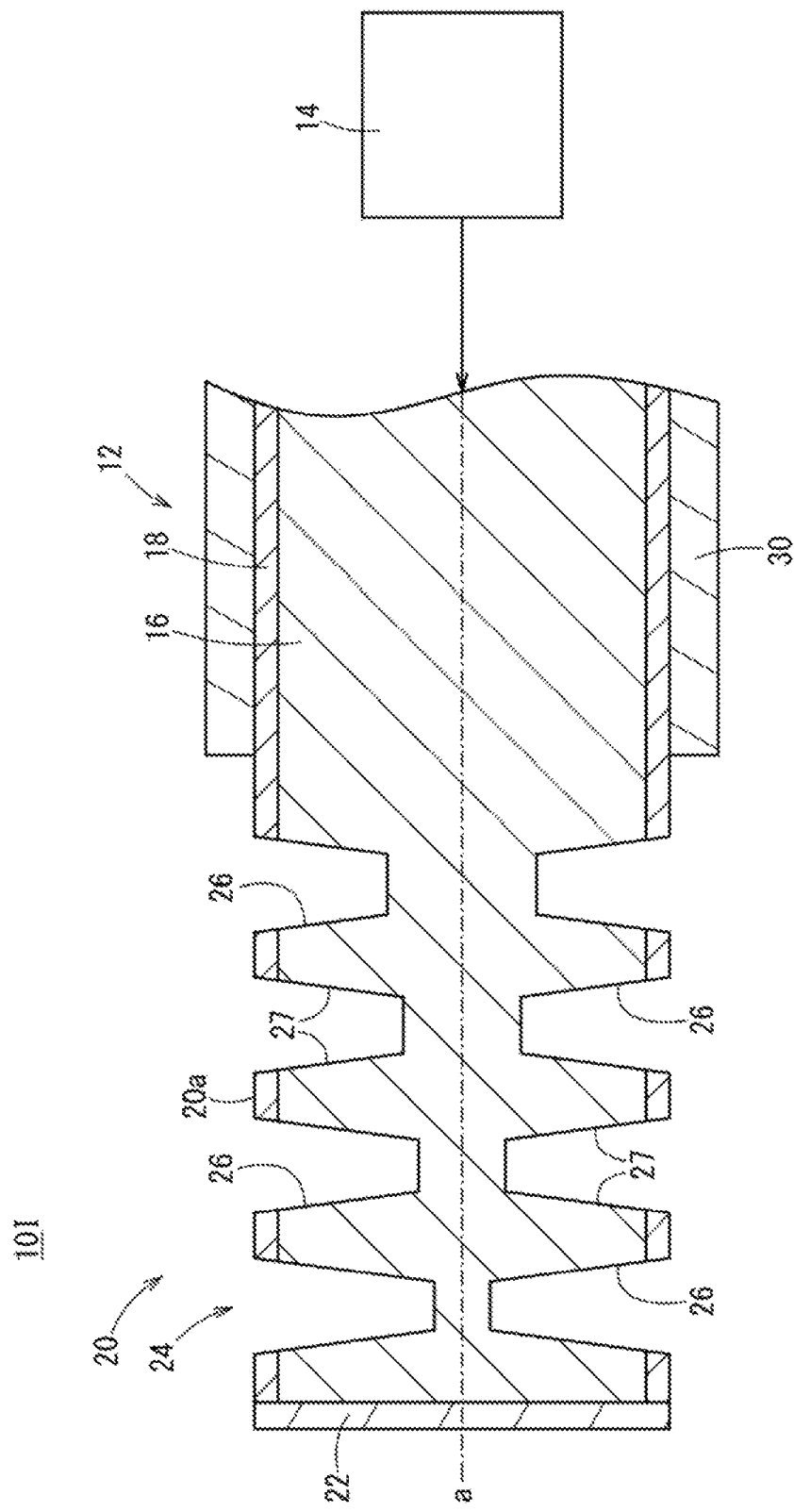
FIG. 11 is a partly-omitted schematic diagram of a treatment device according to a ninth embodiment of the present disclosure.

FIG. 11 is a partly-omitted schematic diagram of a treatment device 10I according to a ninth embodiment of the present disclosure. In the treatment device 10I, a groove structure 24 has plural annular grooves 26 that are formed with the intermediary of intervals in the axial direction of an optical fiber 12 and extend in the circumferential direction, and the depth of the annular groove 26 decreases from the proximal side of the optical fiber 12 toward the distal side.

In this case, the sectional shape of the annular groove 26 can be set to a trapezoidal shape in which the groove width decreases toward a center axis line a as shown in FIG. 11. However the section shape may be set to a V-shape or a U-shape. Alternatively, the sectional shape of the annular groove 26 may be a rectangular shape similarly to the configuration of FIG. 5. Furthermore, the sectional shape of the annular groove 26 may be set to the shape of the annular groove 26 in the above-described treatment devices 100 to 10G.

In a treatment method by use of the treatment device 10I the above-described insertion step is carried out as with the treatment device 10A. Next, in order to carry out a procedure for occlusion for a vein VE, an irradiation step of cauterizing a vein wall by heat attributed to irradiation with laser light is carried out. In this irradiation step, the vein wall is irradiated with the laser light while the treatment device 10I (emitting part 20) is moved in the distal direction in the vein VE (living body lumen). The vein can be occluded by denaturing tissue of the vein wall by the irradiation with the laser light.

In this case, in the treatment device 10I, the depth of the annular groove 26 increases from the proximal side of the optical fiber 12 toward the distal side. For this reason, when the vein wall is irradiated with the laser light while the treatment device 10I is moved in the distal direction in the vein VE, the irradiation intensity of the laser light at each position on the vein wall radiated with the laser light gradually decreases (shows a decrease tendency) along with the elapse of the procedure time. Therefore, excessive temperature rise of the vein wall can be suppressed and the vein wall can be effectively cauterized by heat attributed to the irradiation with the laser light.

In the above-described treatment devices 10A to 10I, the configuration examples are cited in which the depth of the annular groove 26 or the spiral groove 44 increases from the distal side toward the proximal side or from the proximal side toward the distal side. However, the present disclosure is not limited to such configurations. Therefore, the configuration in which the intensities of laser light emitted from the respective grooves differ may be formed by setting the groove depths of the annular grooves 26 or the spiral groove 44 arranged along the axial direction identical (even) and differentiating a shape factor other than the groove depth (for example, aperture width in the axial direction, the angle of the groove forming surface with respect to the center axis line a, etc.). For example, the width and/or area of the aperture part of the groove (annular groove 26 or the like) forming the groove structure 24 may be larger on the proximal side of the optical fiber 12 and decrease toward the distal side. This can decrease the intensity of the laser light toward the distal side.

In the above-described treatment devices 10A to 10I, the clad 18 is provided also at the emitting part 20. However, in modification examples of these treatment devices 10A to 10I, the clad 18 may be not provided at the emitting part 20. In accordance with an exemplary embodiment, the outer circumferential surface of the core 1 may be exposed at the emitting part 20.

The above-described treatment devices 10A to 10I can be configured as devices for various treatments besides the device for treatment of the varicose vein Therefore, the treatment devices 10A to 10I can be applied to treatment of various living body lumens such as artery, lymphatic vessel, bile duct, trachea, esophagus, urethra, and nasal cavity, for example.

The detailed description above describes a treatment device and a living body lumen treatment method for treatment of a living body lumen. The invention is not limited, however, to the precise embodiments and variations described. Various changes, modifications and equivalents can effected by one skilled in the art without departing from the spirit and scope of h invention as defined in the accompanying claims. It is expressly intended that ail such changes, modifications and equivalents which fall within the scope of the claim are embraced by the claims.

What is claimed is:

1. An optical fiber for treatment of a living body lumen, the optical fiber comprising:
    an emitting part configured to emit laser light from a side circumferential surface; and
    two or more annular grooves, the two or more annular grooves being provided in the emitting part at places different in a longitudinal direction of the emitting part, each of the two or more annular grooves having groove forming surfaces having an angle with respect to an axial direction of the optical fiber, and wherein each of the groove forming surfaces in a groove depth direction has at least two surfaces, and wherein the at least two surfaces being different from each other in the angle with respect to the axial direction of the optical fiber.

2. The optical fiber according to claim 1, wherein the two or more annular grooves extend in a circumferential direction of the optical fiber.

3. The optical fiber according to claim 1, wherein a groove surface closer to a center axis line of the optical fiber in the at least two surfaces is smaller than a groove surface farther from the center axis line in the angle with respect to the axial direction of the optical fiber.

4. The optical fiber according to claim 3, wherein a ratio of groove depth of the groove surface closer to the center axis line of the optical fiber in the at least two surfaces to groove depth of the groove surface farther from the center axis line decreases from a proximal side of the optical fiber toward a distal side.

5. The optical fiber according to claim 1, wherein the optical fiber includes a core, and a cladding covering the core, and wherein cladding has a lower refractive index than the core, and wherein the core forms a higher refractive index region and the cladding forms a lower refractive index region; and
    a blocking member on a distal end of the core of the optical fiber.

6. The optical fiber according to claim 1, wherein a width of each of the two or more annular grooves along the axial direction decreases towards a distal end of the optical fiber.

7. A treatment device for treatment of a living body lumen, comprising:
    a laser light source configured to output a laser light; and
    an optical fiber having an emitting part configured to emit the laser light from a side circumferential surface, the optical fiber comprising:
        two or more annular grooves, the two or more annular grooves being provided in the emitting part at places different in a longitudinal direction of the emitting part, each of the two or more annular grooves having groove forming surfaces having an angle with respect to an axial direction of the optical fiber, and wherein each of the groove forming surfaces in a groove depth direction has at least two surfaces, and wherein the at least two surfaces being different from each other in the angle with respect to the axial direction of the optical fiber;
    a maximum region of intensity of the laser light emitted from the emitting part is located on a first end side relative to a center position in the longitudinal direction of the emitting part; and
    an intensity of the laser light emitted from the emitting part on a second end side of the emitting part relative to a position of the maximum region decreases toward the second end side.

8. The treatment device according to claim 7, wherein a groove surface closer to a center axis line of the optical fiber in the at least two surfaces is larger than a groove surface farther from the center axis line in the angle with respect to the axial direction of the optical fiber.

9. The treatment device according to claim 8, wherein a ratio of groove depth of the groove surface closer to the center axis line of the optical fiber in the at least two surfaces to groove depth of the groove surface farther from the center axis line decreases from a proximal side of the optical fiber toward a distal side.

10. The treatment device according to claim 7, wherein the optical fiber includes a core, and a cladding covering the core.

11. The treatment device according to claim 10, wherein cladding has a lower refractive index than the core, and wherein the core forms a higher refractive index region and the cladding forms a lower refractive index region.

12. The treatment device according to claim 11, comprising:
a blocking member on a distal end of the core of the optical fiber.

13. The treatment device according to claim 7, wherein the two or more annular grooves extend in a circumferential direction of the optical fiber.

14. The treatment device according to claim 7, wherein a width of each of the two or more annular grooves along the axial direction decreases towards a distal end of the optical fiber.

15. A living body lumen treatment method comprising:
inserting an elongated-shaped treatment device having a laser light source configured to output a laser light and an optical fiber an emitting part configured to emit laser light from a side circumferential surface into a living body lumen, the elongated-shaped treatment device including an emitting part configured to emit the laser light from a side circumferential surface, and two or more annular grooves, the two or more annular grooves being provided in the emitting part at places different in a longitudinal direction of the emitting part, each of the two or more annular grooves having groove forming surfaces having an angle with respect to an axial direction of the optical fiber, and wherein each of the groove forming surfaces in a groove depth direction has at least two surfaces, and wherein the at least two surfaces being different from each other in the angle with respect to the axial direction of the optical fiber; and
irradiating a wall of the living body lumen with the laser light while the treatment device is moved in a longitudinal direction in the living body lumen,
wherein in the irradiating, irradiation with the laser light is carried out in such a manner that a temperature rise rate at each position on the wall of the living body lumen irradiated with the laser light decreases along with elapse of a procedure time.

16. The method according to claim 15, wherein the elongated-shaped treatment device comprises:
different intensities of the laser light being emitted from the two or more annular grooves adjacent to each other.

17. The method according to claim 15, wherein the elongated-shaped treatment device comprises:
a maximum region of intensity of the laser light emitted from the emitting part is located on a first end side relative to a center position in the longitudinal direction of the emitting part; and
an intensity of the laser light emitted from the emitting part on a second end side of the emitting part relative to a position of the maximum region decreases toward the second end side.

18. A living body lumen treatment method comprising:
inserting an elongated-shaped treatment device having a laser light source configured to output a laser light and an optical fiber having an emitting part configured to emit laser light from a side circumferential surface into a living body lumen, the elongated-shaped treatment device including an emitting part configured to emit the laser light from a side circumferential surface, and two or more annular grooves, the two or more annular grooves being provided in the emitting part at places different in a longitudinal direction of the emitting part, each of the two or more annular grooves having groove forming surfaces having an angle with respect to an axial direction of the optical fiber, and wherein each of the groove forming surfaces in a groove depth direction has at least two surfaces, and wherein the at least two surfaces being different from each other in the angle with respect to the axial direction of the optical fiber; and
irradiating a wall of the living body lumen with the laser light while the treatment device is moved in a longitudinal direction in the living body lumen,
wherein in the irradiating, intensity of the laser light at each position on the wall of the living body lumen irradiated with the laser light shows a decrease tendency along with elapse of a procedure time after the intensity reaches a maximum region.

19. The method according to claim 18, wherein the elongated-shaped treatment device comprises:
different intensities of the laser light emitted from the two or more grooves adjacent to each other.

20. The method according to claim 18, wherein the elongated-shaped treatment device comprises:
a maximum region of intensity of the laser light emitted from the emitting part is located on a first end side relative to a center position in the longitudinal direction of the emitting part; and
an intensity of the laser light emitted from the emitting part on a second end side of the emitting part relative to a position of the maximum region decreases toward the second end side.

* * * * *